United States Patent
Wycoki

[19]

[11] Patent Number: 6,010,474
[45] Date of Patent: Jan. 4, 2000

[54] ORTHOPEDIC BRACE FOR LEGS

[76] Inventor: Michael Wycoki, 245 Center St., Jupiter, Fla. 33458

[21] Appl. No.: 08/870,245

[22] Filed: Jun. 6, 1997

[51] Int. Cl.$^7$ ....................................................... A61F 5/00
[52] U.S. Cl. .............................................. 602/23; 602/26
[58] Field of Search ........................... 602/15, 16, 23–26; 623/27–29, 32, 38, 39

[56] References Cited

U.S. PATENT DOCUMENTS

| | | | |
|---|---|---|---|
| 2,522,853 | 9/1950 | Black ...................................... | 602/23 X |
| 3,026,869 | 3/1962 | Peach ....................................... | 602/16 |
| 3,230,952 | 1/1966 | Terron ...................................... | 602/16 |
| 3,316,900 | 5/1967 | Young .................................... | 602/23 X |
| 4,865,024 | 9/1989 | Hensley et al. ............................ | 602/16 |
| 4,947,834 | 8/1990 | Kartheus et al. . | |
| 5,302,169 | 4/1994 | Taylor . | |
| 5,342,288 | 8/1994 | Lee et al. ..................................... | 602/5 |
| 5,344,390 | 9/1994 | Motloch .................................... | 602/23 |
| 5,360,394 | 11/1994 | Christensen ............................... | 602/26 |
| 5,395,304 | 3/1995 | Tarr et al. ................................. | 602/26 |
| 5,400,806 | 3/1995 | Taylor . | |
| 5,443,444 | 8/1995 | Pruyssers .............................. | 602/16 X |

Primary Examiner—Richard J. Apley
Assistant Examiner—Denise Pothier
Attorney, Agent, or Firm—Quarles & Brady

[57] ABSTRACT

A medical brace is disclosed that is arranged to transfer weight bearing forces during walking past the patient's knee to the patient's thigh and pelvic infrastructure. The brace can include a strut assembly that permits bending of the knee while biasing the knee toward extension. The strut assembly can also be equipped with a strap for relieving pressure from an affected compartment of the knee and transferring the pressure through the strut assembly to the thigh. The strut assembly also transfers force from a shoe and heel bridge assembly past the knee to a thigh cuff that is equipped with inflatable bladder to control relative weight distribution in the above knee region. The shoe and heel bridge assembly can also provide a spring plate to supply lifting bias to the heel, thereby aiding on the transition from the heel strike to the toe-off phase of walking.

8 Claims, 5 Drawing Sheets

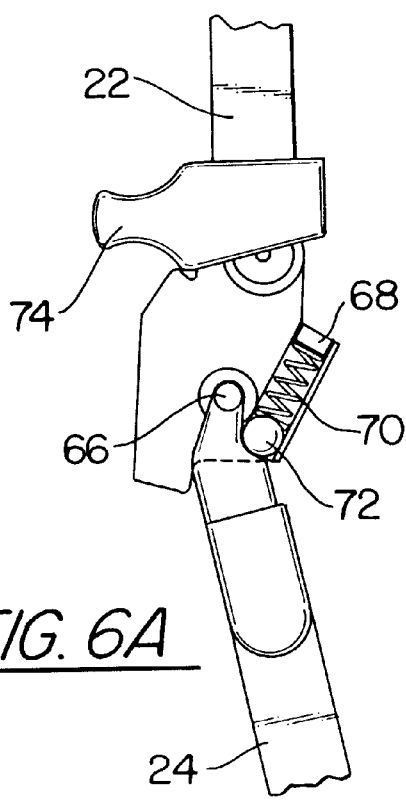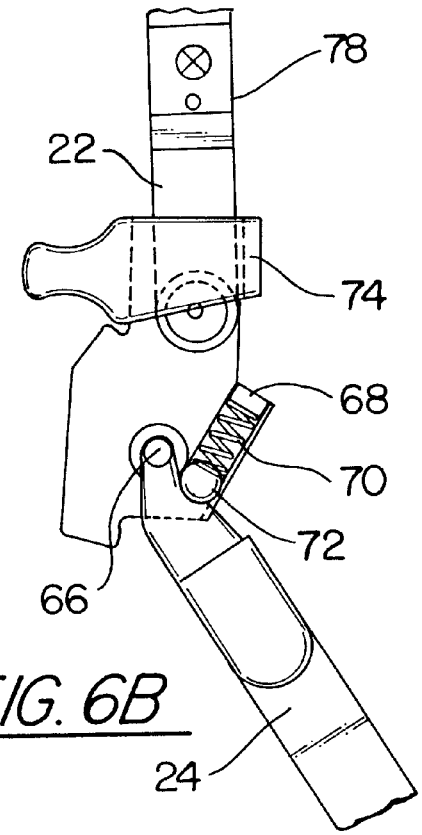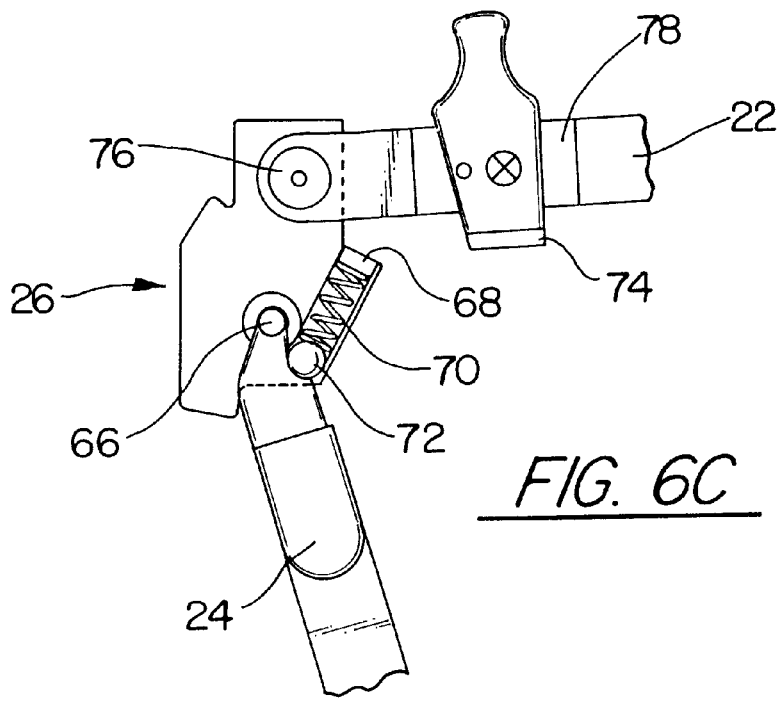

ORTHOPEDIC BRACE FOR LEGS

FIELD OF THE INVENTION

The invention relates to orthopedic braces. More particularly, the invention relates to orthopedic braces for assisting patients with various lower extremity maladies, particularly knee conditions.

BACKGROUND OF THE INVENTION

A brief review of walking mechanics and knee anatomy will aid in an appreciation of the invention. The typical human walking cycle can be considered to begin with a heel strike to the ground, followed by a mid-stance phase in which the front of the foot lowers to the ground, pivoting about the grounded heel. The gait then transitions to a toe-off phase, in which the heel is lifted with an associated forward motion of the leg and body on the ball and toes of the foot. Ultimately, the foot is completely lifted from the ground and swung forward in a swing-through phase to the next heel strike. The other foot undertakes the same cycle of motion in a generally coordinated manner to provide forward locomotion.

During this complex motion, each knee transitions from a relatively straight extension at the heel strike to a rearward bend, or flexion, through the toe-off phase and returns to extension during the final swing-through phase. During the cycle, the weight of the patient is borne through the knee to varying degrees.

The human knee system can suffer a number of diseases that can affect the patient's ability to bear this weight and walk without pain. Perhaps the most often diagnosed disease is arthritis, which can affect the knee's medial compartment, located toward the body center, or the lateral compartment, located opposite the medial compartment on the outer side of the knee. In some circumstances, the patellofemoral compartment is also affected. The malfunction frequently occurs in one compartment, but some cases involve arthritis in two or three compartments of the knee.

A number of braces have been developed in the past to address uni-compartmental osteoarthritis by shifting the distribution of the pressure on the knee during walking to the non-diseased compartment of the knee. For example, U.S. Pat. No. 5,302,169 to Taylor discloses a knee brace that adjustably braces the leg in a lateral or medial inclination to transfer pressure from the affected compartment to the relatively healthier compartment. Depending on the compartment to be aided, the brace can induce varus (bow-leggedness) or vulgas (knock-kneedness). The Taylor device and other known devices focus on controlling the distribution of forces within the knee system, using the calf and thigh directly adjacent the joint to leverage the desired force transfers among the knee compartments.

While these devices have enjoyed some success in treating uni-compartmental conditions, they are incapable of addressing bi- or tri-compartmental maladies. Because of the compartmental transfer approach to the design of these prior devices, a healthy compartment of the knee is required to receive and bear the transferred pressure.

A brace providing substantial knee isolation of the knee from weight while permitting walking is desirable. Such brace can provide a number of advantages. It can be universally applied to all varieties of uni-compartmental conditions as well as bi- and tri-compartmental conditions. Knee isolation during walking can also encourage exercise.

Exercise, particularly low impact activity such as water exercise, has been found to provide numerous health benefits, especially when contrasted to sedentary lifestyle. Yet, many arthritic patients are caught in the physical dilemma that their condition prevents them from being sufficiently mobile to obtain the necessary exercise at remote facilities, such as aquatic exercise centers. Traditional walking aids, such as crutches canes and walkers, can often discourage patients from moving to exercise, perpetuating the problem and culminating in the need for corrective surgery.

SUMMARY OF THE INVENTION

It is therefore an object of the invention to provide an orthopedic brace that replaces crutches, walkers, canes or other walking aides in orthopedic or injured patients.

It is another object of the invention to provide a supportive device that can be worn under loose clothing.

It is a further object of the invention to provide an orthopedic brace for knee conditions that decreases stress about the knee system.

It is an even further object of the invention to improve walking function in arthritic patients to encourage therapeutic exercise to increase overall health, including such benefits as increased general cardiac output, reduced cholesterol levels and blood pressure, and improved mental health.

It is yet another object of the invention to provide a brace that is universally applicable to single and multiple compartment knee conditions.

It is still another object of the invention to provide a brace that assists walking for patients with other lower extremity conditions of the foot, tibia, femur or hip.

These and other objects of the invention are achieved by an orthopedic brace that transfers weight past the knee and other lower extremity components to the pelvic region and the greater trochanteric area of the femur during walking. The brace generally includes an above knee attachment for securing the brace to the patient's thigh, a below ankle attachment for securing the brace preferably to the patient's foot and a transfer mechanism connected between the attachments for transferring the weight bearing forces during walking from the foot, past the affected knee or other area, to the thigh and pelvic infrastructure.

The transfer mechanism preferably includes a pair of strut assemblies connected between the above knee attachment and the below ankle attachment. The strut assemblies can each include a hinge between an upper strut and a lower strut to permit knee bending.

According to an aspect of the invention, the above knee attachment is constructed as a removable thigh cuff generally fitted to the patient's thigh to generally transfer forces to the soft tissue of the entire thigh and preferably shaped to enhance force transfer to the ischium and pelvic pillars and to the greater trochanter region. The thigh cuff is also preferably equipped with a number of inflatable bladders to adjust the degree of engagement with different portions of the thigh and pelvic structure. In this way, the user can customize the distribution of forces to the appropriate sections of the thigh and pelvis.

The preferred thigh cuff can mount to the patient through a slit along the front of the cuff. Once mounted, the cuff can be secured with a series of fixed length straps to insure uniform engagement with the thigh over repeated applications.

The amount of weight transfer is a function of the degree to which the knee is locked from further flexion. Force transference to the above knee region occurs most significantly when the brace reaches the limit of flexion, which can be established by a physical stop in the strut assembly. However, such construction tends to transfer relatively little force to the above knee region before the flexion limit of the brace and then applies the transferred forces to the above knee region as an impulse upon reaching the flexion limit of the brace.

According to another aspect of the invention, the pivoting of the struts about the hinge—and the associated knee bend—is resisted by a spring mechanism. The gradually increasing spring resistance during flexion serves as gradually increasing series of "stops" and begins the force transference earlier in flexion in gradually increasing fashion so that impulsive force transfer is avoided. The initial spring tension can be adjustable so that the amount and manner of force transference can be controlled to suit patient preferences and needs.

Each strut assembly can also provide, near the spring biased hinge, a second hinge that permits unrestricted bending of the knee for sitting and the like. The second hinge can be fixed during walking by a sliding lock that can be selectively moved by the patient to activate the second hinge when sitting or other free knee motion is desired.

According to a further aspect of the invention, the below ankle attachment is preferably formed in a shoe structure that includes a heel bridge laterally spanning the sole of the shoe at a heel location and connecting to the bottom of each of the strut assemblies. The assembly effectively locks the ankle joint so that weight is transferred up the struts to the thigh. In this manner, weight bearing forces along the bottom of the foot, and particularly at the heel, are transmitted past the lower leg and knee to the thigh, significantly relieving the knee of pressure during walking or standing. The shoe sole can further provide a spring plate secured at a front end of the sole to upwardly bias the heel bridge and patient's heel for aiding in transitioning from the heel strike phase to the toe-off phase.

Thus, the medical brace of the invention provides a support to substantially reduce the exposure of an arthritic or otherwise affected knee or other lower extremity component to weight bearing forces, permitting assisted walking and the related therapeutic and other advantages.

BRIEF DESCRIPTION OF THE DRAWINGS

These and other aspects of the invention will become more apparent from a reading of the following detailed description in conjunction with the accompanying drawings, in which:

FIG. 6A is a partial side elevational view of a preferred hinge mechanism of the medical brace during knee extension, FIG. 6B is a partial side elevational view thereof when the knee is in flexion and FIG. 6C is a partial side elevational view of the hinge mechanism released to permit full knee motion.

DETAILED DESCRIPTION OF EMBODIMENTS OF THE INVENTION

The invention relates generally to medical braces, but is particularly concerned with relieving the knee joint from a substantial portion of weight bearing forces during walking and allocating these forces directly to the thigh and pelvic infrastructure through the ischium. The thigh and pelvic region will at times be collectively referred to as the above knee region herein. The brace can have other applications in aiding patients with lower body ailments in the various regions from the hips to the feet, but focus herein will be directed primarily to the application of the invention to assisting patients with knee conditions, such as arthritis or other destructive agents of the knee.

The brace of the invention generally includes a below ankle attachment for securing the brace to the patient at or below the ankle, preferably at the foot; an above knee attachment for securing the brace to the patient above the knee, preferably at the thigh; and a transfer mechanism in between for transferring forces between the attachments, while permitting controlled bending of the knee.

Figure 1:
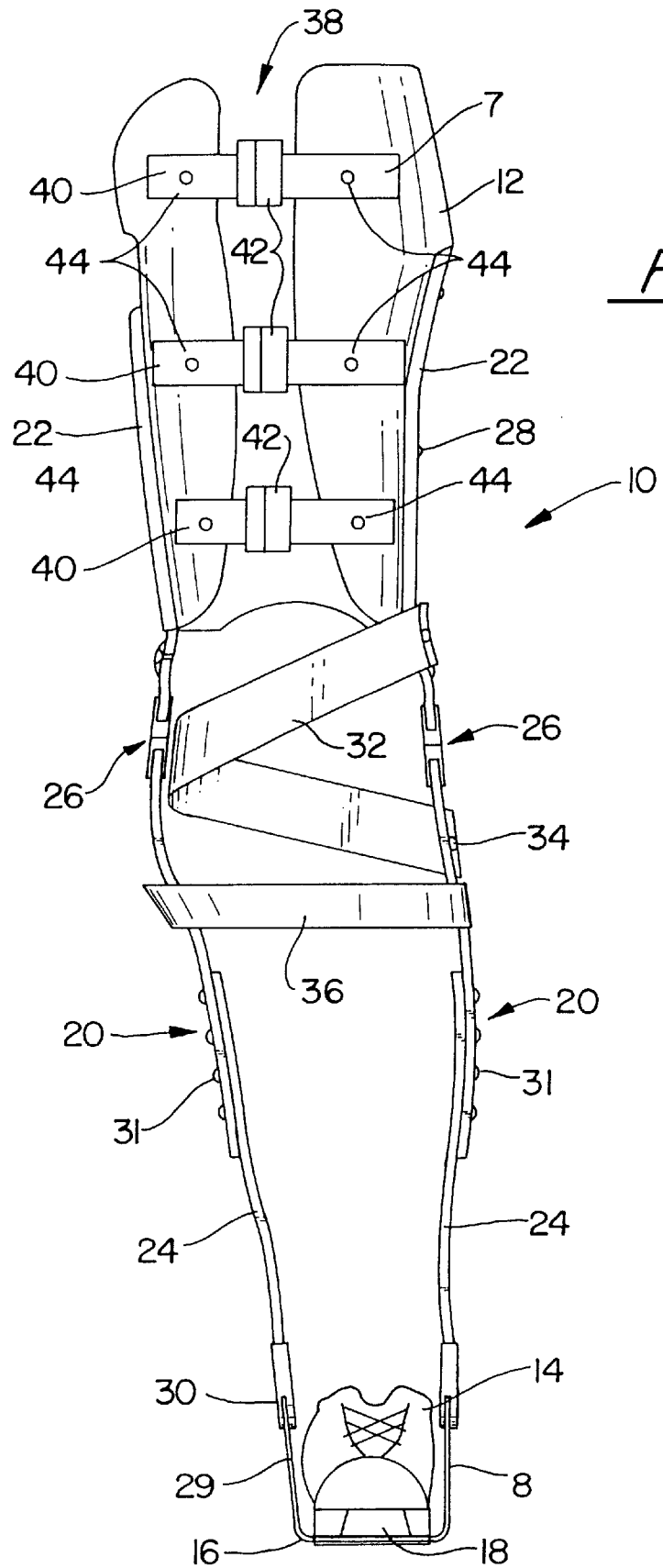
FIG. 1 is a front elevational view of an embodiment of a medical brace according to the invention.

Referring to the drawings generally and particularly to FIG. 1, the invention can be embodied in a knee brace 10 having a thigh cuff 12 that can serve as the upper attachment. The lower attachment can include a support shoe 14 providing a heel bridge 16, embedded in the sole 18 of the support shoe 14. The transfer mechanism can include a pair of strut assemblies 20 secured to the heel bridge 16 and to the thigh cuff 12 for transferring weight bearing forces from the heel bridge 16 to the thigh cuff 12 and thereby generally relieving the knee (not shown) of the weight bearing forces.

Various anatomical structures of the patient, such as the knee alone, are referenced in this description but are not shown to aid in clarity of the drawing. It is understood that these body components are well known to one skilled in the art.

Each strut assembly 20 preferably includes an upper strut 22 and a lower strut 24 joined by a hinge assembly 26 that permits pivoting of the upper struts 22 and the lower struts 24 relative to each other, and associated bending of the patient's knee. Each upper strut 22 can be secured to the thigh cuff 12 by fasteners, such as screws 28, and the mounting position of each upper strut 22 to the thigh cuff 12 can be customized to the size and shape of the patient's leg (not shown).

Each lower strut 24 is fastened to a tang 29 of the heel bridge 16 by a lockable hinge 30 that allows adjustment of the plantarflexion and dorsiflexion of the ankle joint. The lower strut 24 can also be equipped with two sections secured by screws 31 to permit customized adjustment of the length of the lower strut 24.

The strut assemblies 20 can optionally be equipped with a strap 32 that can be attached to urge the knee region laterally or medially to transfer pressure to the thigh and pelvic region. The strap 32 attaches to the strut assembly 20 on the side of the brace directly opposite the deformity and can be secured by screws 34 or other fasteners. The strap 32 allows unloading of an affected medial or lateral joint space (not shown), but unlike prior devices, the transferred weight is not routed to the less-affected medial or lateral compartment (not shown), but rather to the above knee region through the thigh cuff 12 through the attached strut assembly 20.

A second strap 36 below the knee joint at the tibial metaphysis (not shown) can be provided to stabilize the brace 10 from medial or lateral shifting of the leg or widening of the brace 10. The struts 22, 24 can also be custom-shaped to the contours of the patient's legs, as shown for example.

The thigh cuff 12 is preferably sliced along its anterior face to provide a slit or opening 38 for mounting and dismounting. A thin polyethylene insert (not shown) can be used to cover the slit or opening 38 after placing the thigh inside the cuff 12 to complete the quadrilateral nature of the thigh cuff 12 and to avoid pinching the skin at the slit or opening 38 of the thigh cuff 12 and anterior migration of the thigh soft tissue toward the slit or opening 38.

A plurality of straps 40 with releasable buckles 42 can be provided to secure the thigh cuff 12. The straps 40 are preferably of adjustable but non-stretchable length that is initially custom set for the patient to maintain uniform tightness of the thigh cuff 12 with each mounting. The straps 40 can be secured on each side of the slit or opening 38 by screws 44 or the like. The straps 40 can allow adjustability, but unlike hook and loop-type securement straps, can maintain the length and associated tightness of the thigh cuff 12 once adjusted, easing re-application of the brace 10.

Figure 2:
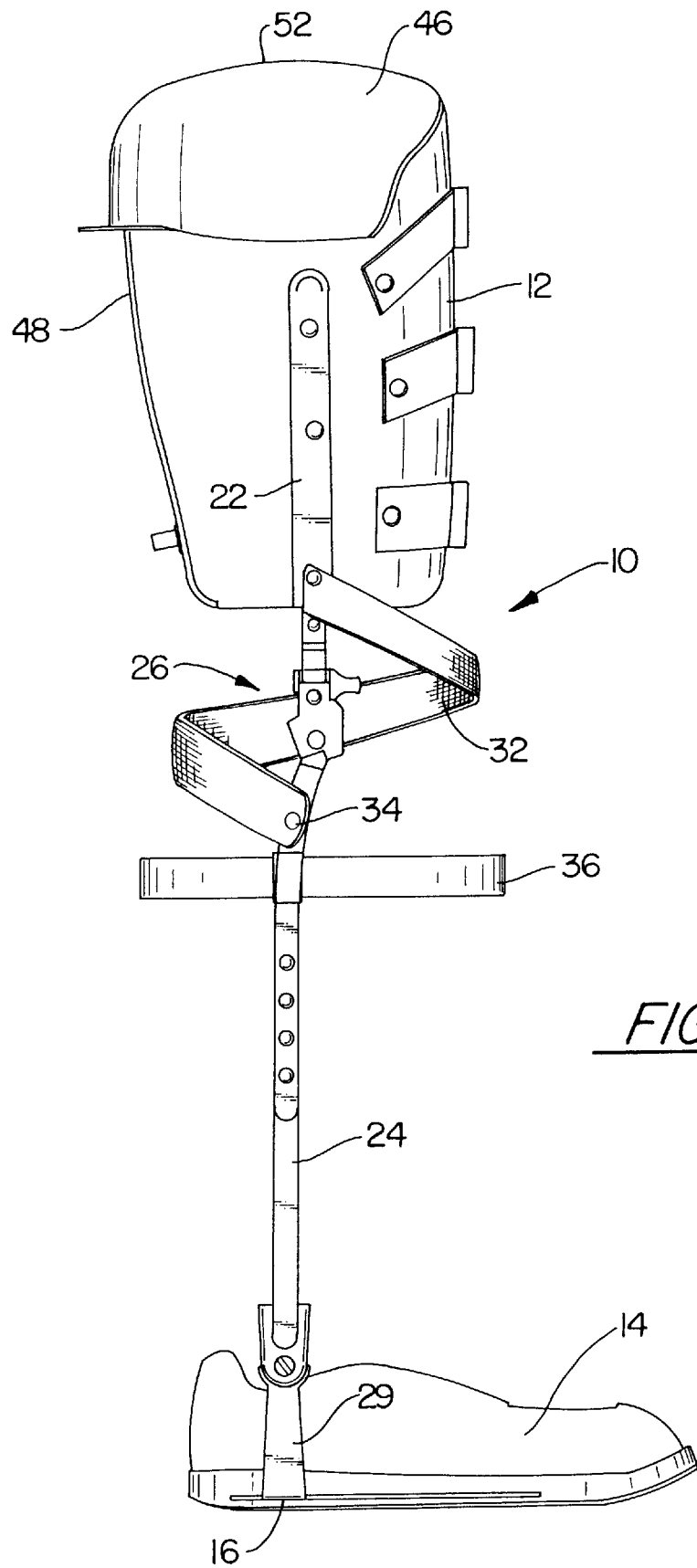
FIG. 2 is a medial elevational view thereof.
Figure 3:
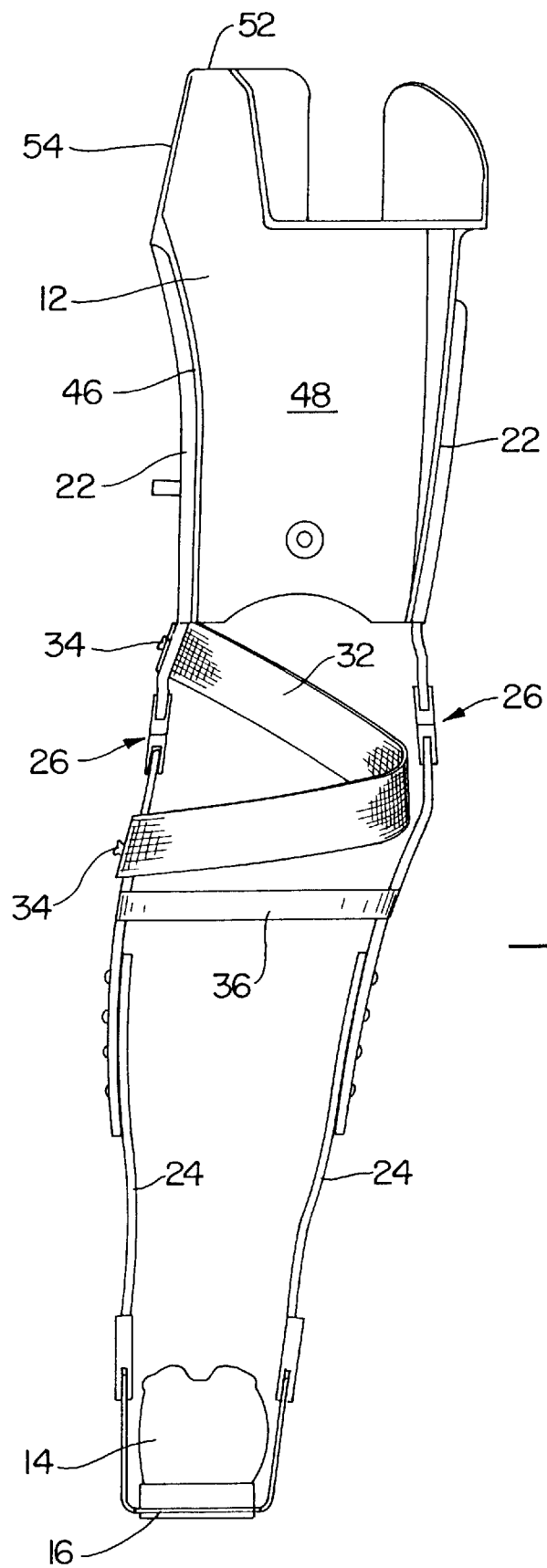
FIG. 3 is a rear elevational view thereof.

Referring to FIGS. 2 and 3 together, the thigh cuff 12 is preferably shaped to allocate weight bearing forces to various portions of the above knee region. The thigh cuff is preferably custom shaped to the patient's leg to engage all surfaces of the thigh and transfer forces thereto, utilizing the somewhat conical geometry of the thigh region. The lateral aspect 46 of the thigh cuff 12 is preferably custom-shaped to extend to and engage the greater trochanter area of the patient (not shown), while the posterior aspect 48 preferably extends to be engaged by the patient's ischium (not shown).

The thigh cuff 12 preferably has a highest point 52 on the lateral aspect of the thigh as it migrates and meets with the greater trochanter area and its soft tissue. The thigh cuff 12 preferably provides a medial flare 54 of the lateral wall 46 to enhance engagement with the greater trochanter region and gluteal area and thereby allocate a greater portion of the transferred forces to these areas than to the anterior or medial areas of the thigh. The anterior portion of the thigh cuff 12 slopes medially, thereby avoiding contact with the peroneal area of the patient (not shown).

The posterior aspect 48 preferably forms a posterior platform, preferably customized to terminate at the ischium and provide a seat against which the ischium and the associated pelvic infrastructure can rest. The ischial engagement can be utilized to place substantially all the weight bearing forces in the pelvic pillars and relieve the entire lower extremity of the forces.

The material of the thigh cuff 12 is preferably made of a pliable plastic and is preferably custom-shaped to the patient's thigh, using such techniques as simple tracing and casting. Alternative compositions, such as graphite-based or other moldable materials, are also possible.

Figure 4A:
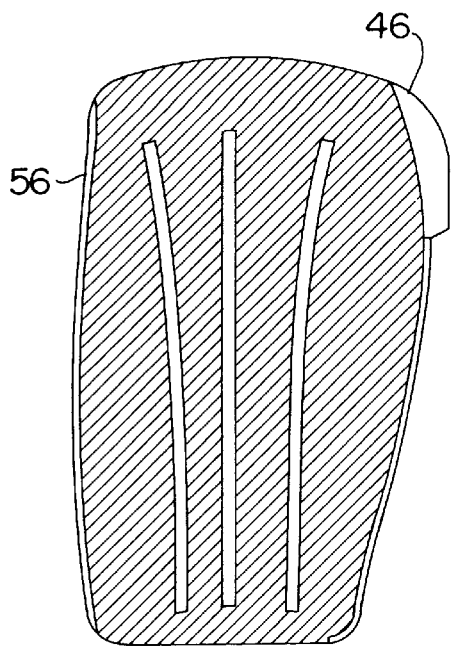
FIG. 4A is an elevational view of a preferred lateral inflatable insert for the upper attachment.
Figure 4B:
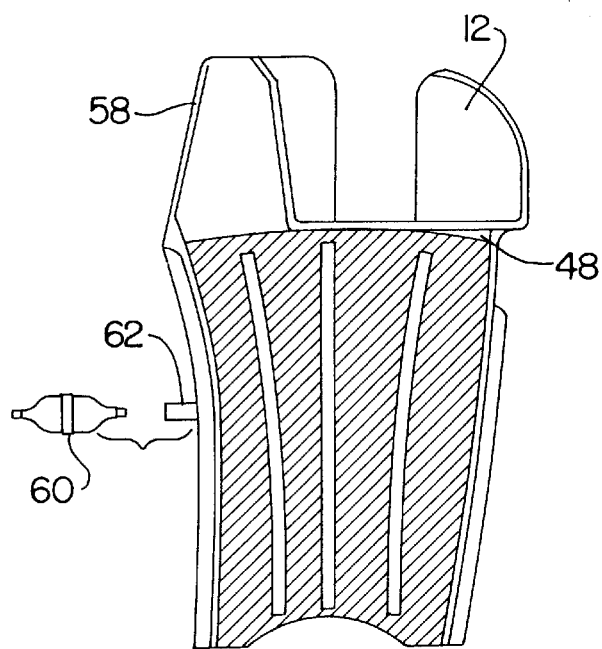
FIG. 4B is an elevation view of a preferred posterior inflatable insert for the upper attachment.

To further fine-tune the proper distribution of weight among the above knee regions, the thigh cuff 12 can allow the insertion of two inflatable bladders 56, 58, as shown in FIGS. 4A and 4B. A first bladder 56 is preferably mounted along the lateral aspect 46 of the thigh cuff, and the second bladder 58 is mounted in the posterior region 48.

The bladders 56, 58 can be inflated by the patient using a hand pump 60 through inflation ports 62 to customize the degree of engagement between the thigh cuff 12 and the various parts of the above knee region, thereby adjusting the allocation of weight to suit the comfort and desires of the patient. For example, discomfort in area of the ischial engagement with the rear platform could be alleviated by inflating the lateral bladder to increase engagement with and force transference to the lateral trochanter region while urging soft tissue rearward to further cushion the ischial engagement.

The inflatables 56, 58 are preferably custom-made depending on the shape of the patient's thigh and also are adjustably attachable to allow specific placement by the patient. The bladders 56, 58 can be attached and adjusted in the cuff 12 by hook and loop-type material or other removable fasteners (not shown).

Figure 5A:
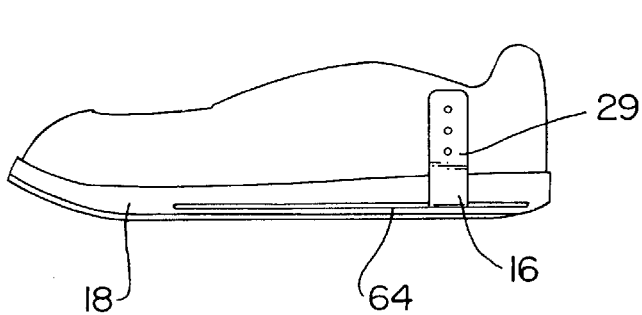
FIG. 5A is a side elevational view of a preferred configuration of the lower attachment according to the invention.
Figure 5B:
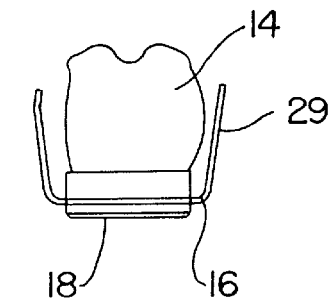
FIG. 5B is a rear elevational view thereof.
Figure 5C:
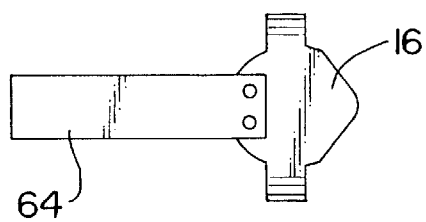
FIG. 5C is a bottom plan view of a preferred heel bridge and spring plate assembly for use with the lower attachment.

Referring to FIGS. 5A, 5B and 5C, the below ankle attachment preferably includes the heel bridge 16 in combination with the support shoe 14, which can be constructed in a variety of styles, including a laced top, a slip-on, a boot, a high-top or other footwear extending above the ankle, or a sandal, and preferably has a thick sole 18.

The heel bridge 16 spans the width of the heel of the support shoe 14, and together the heel bridge and shoe 14 fix the ankle (not shown). The heel bridge tangs 29 can be set with 10–15° of dorsiflexion relative to the lower struts (See FIG. 1) to assist in the swing-through phase of gait. The dorsiflexion can also be adjusted to the patient's need.

The ankle fixation provided by the shoe 14 and heel bridge 16 serve not only to ensure weight transference away from the lower leg but also to stabilize the brace. The preferred construction substantially prohibits rotation or other migration of the brace relative to the leg which can otherwise undermine the support and weight transference function and benefit of the brace.

The heel bridge 16 is preferably supplemented with a spring plate 64 that preferably continues into the mid portion of the shoe sole 18, ending proximate the location of the metatarsals (not shown). The sole 18 is preferably thick enough to accept the heel bridge 16 and the spring plate 64.

This spring plate 64 is flexible and allows the patient to store energy during the heel strike and mid-stance phases. The energy is released in the toe-off phase to assist with the swing-through portion of gait.

Referring to FIGS. 6A, 6B and 6C, the hinge assembly 26 of each strut assembly can be constructed to control knee flexion and extension during walking and permit full knee motion for sitting or any functional positioning of the knee requiring greater than 20°–25° of flexion. A primary hinge 66 preferably allows knee bending from 0° to an adjustably set limit of, for example, 20°–25° of motion.

The hinge mechanism is intended to operate under the principle that force transference to the above knee region is a function of the degree to which the knee is "locked" or prevented from further flexion. Until the flexion is stopped by a limiting abutment of the strut assembly, force transference is minimal. If flexion is resisted, but not stopped, such as by a spring, some force transference proportions to the amount of resistance. Upon locking at the abutment, substantially all forces are transferred.

In order to avoid an impulsive leap in force transfer at the abutment, a variable locking mechanism to control the degree and manner of flexion and force transference over the flexion range can be provided to gradually increase the degree of force transference as flexion increases toward the physical limit. The locking mechanism can include a spring 70 that provides progressive resistance to flexion and a tensioning screw 68 to adjust the initial tension in the spring. A ball bearing 72 is preferably provided to smoothly interface the pivoting lower struts 24 with the spring 70.

The spring 70 is preferably selected and arranged to provide notable resistance in the 10° to 25° range of flexion, thereby gently increasing weight transfer as the lower strut rotates toward the flexion limit.

The tensioning screw can be used to control the balance between flexion range of the knee and weight support by the above knee region. A patient may desire greater and prompter weight support by the above knee region and select a rigid setting in which flexion limit is reached quickly, for example, at 5° or less; such setting results in a relatively stiff gait. Alternatively, a patient may desire a greater degree of flexion and a more natural gait, and therefore select a relaxed setting in which force transference occurs more gradually along a greater range of flexion.

A sliding block 74 permits pivoting about a second hinge 76, allowing the patient to have full extension and flexion such as when in a sitting position. The sliding block 74 is easily moved to the unlocked position as shown in FIG. 6C, and returned by gravity to the locked position, as shown in FIGS. 6A and 6B when the patient stands. Alternatively, the sliding block 74 can be releasably secured, such as by a ramped locking mount 78, in the unlocked position to allow full motion when desired without removal of the brace or continual unlocking.

The medical brace thus described can be used for any medical diagnosis that requires unloading of the knee, and to a lesser extent, the ankle joint, tibial component or the hip. It is specifically indicated for bi- and tri-compartmental arthritis of the knee. The indications are broader than those of prior art braces which are typically only beneficial in a uni-compartmental arthrosis with varus or valgus. The brace of the invention allows for unloading both compartments of the knee medially and laterally, and to some extent, the patella femoral joint as well. Additional uses include osteochondritis desiccans, fractures of the distal femur, or proximal tibia and fibula, as well as arthritis of the hip.

Although preferred embodiments of the invention have been described with particular detail to enable one skilled in the art to make and use the invention, alternatives within the scope of the invention but not particularly denoted are now likely to be apparent to the skilled artisan. The scope of the invention should therefore be determined in accordance with the law from the following claims and not limited to the examples set forth above.

I claim:

1. A medical brace, comprising:
    a below ankle attachment for securing said brace to a patient below the patient's ankle, said below ankle attachment including a support shoe for the patient's foot and a heel bridge spanning the shoe and connecting to each of a pair of strut assemblies;
    a thigh cuff for securing said brace to said patient above the patient's knee, said thigh cuff having a rear portion extending upwardly for engagement with soft tissue surrounding the patient's ischium and an outer side portion extending to the patient's greater trochanter region; and,
    a mechanism connecting said below ankle attachment and said thigh cuff for transferring loads past the patient's knee during walking, said mechanism permitting bending of the patient's knee for sitting, said mechanism including:
        said pair of strut assemblies for extending along the patient's leg on opposite sides of the leg, each strut assembly sized and configured to be pivotable proximate the knee to permit bending of the knee during walking,
        each of said strut assemblies including a hinge pivotally connecting an upper and a lower strut, said hinge located and configured for permitting bending proximate the knee,
        each of said strut assemblies further including a spring mechanism for resisting bending of said strut assembly, said spring mechanism having an adjustable resistance,
        each of said strut assemblies further including a second hinge for permitting bending proximate the patient's knee and a sliding lock for selectively permitting pivoting about the second hinge for substantial knee bend during sitting.

2. The medical brace according to claim 1, wherein the thigh cuff is equipped with at least one inflatable bladder to adjustably controlling the degree of engagement with the patient's thigh.

3. The medical brace according to claim 2, wherein the thigh cuff is equipped with an inflatable bladder along the outer side portion of the cuff and an inflatable bladder along the rear portion of the cuff for adjustably controlling the relative distribution of weight along the patient's thigh and pelvic infrastructure.

4. The medical brace according to claim 3, wherein the thigh cuff has a slit along its front to permit removable mounting on the patient's thigh.

5. The medical brace according to claim 4, wherein the thigh cuff is secured by a plurality of straps spanning the cuff slit.

6. The medical brace according to claim 5, wherein the straps are fixed on opposite sides of the slit and secured by buckles to a fixed, predetermined length.

7. The medical brace according to claim 1, wherein the support shoe includes a sole and a spring plate configured in the sole to provide resilient upward bias to the heel bridge.

8. The medical brace according to claim 1, wherein the thigh cuff is constructed of moldable material.

* * * * *